United States Patent [19]

Jansen, Jr.

[11] Patent Number: 4,945,083
[45] Date of Patent: Jul. 31, 1990

[54] SAFE ORAL FOLIC-ACID-CONTAINING VITAMIN PREPARATION

[76] Inventor: Christian J. Jansen, Jr., 6350 Glen Coe Dr., Indianapolis, Ind. 46260

[21] Appl. No.: 305,422

[22] Filed: Feb. 1, 1989

Related U.S. Application Data

[63] Continuation of Ser. No. 869,985, Jun. 3, 1986, abandoned, which is a continuation of Ser. No. 662,813, Oct. 22, 1984, abandoned, which is a continuation of Ser. No. 500,228, Jun. 1, 1983, abandoned, which is a continuation of Ser. No. 268,744, Jun. 1, 1981, abandoned, which is a continuation of Ser. No. 826,814, Aug. 22, 1977, abandoned, which is a continuation of Ser. No. 650,887, Jan. 21, 1976, abandoned, which is a continuation of Ser. No. 57,302, Jul. 22, 1970, abandoned.

[51] Int. Cl.$^5$ .................... A61K 31/70; A61K 31/50;
  A61K 31/495
[52] U.S. Cl. ...................... 514/52; 514/249;
  514/814
[58] Field of Search .................. 514/814, 249, 82, 80,
  514/52

[56] References Cited

U.S. PATENT DOCUMENTS

| | | | |
|---|---|---|---|
| 2,748,054 | 5/1956 | Jurist | 424/201 |
| 2,804,423 | 8/1957 | Sahyun | 424/201 |
| 4,053,593 | 10/1977 | Frumoff | 424/201 |

OTHER PUBLICATIONS

The Pharmacological Basis of Therapeutics-5th ed--Goodman et al., pp. 1324-1349 (1975).
Recommended Diebary Allowance 8th Rev. Ed. (1974), National Academy of Science, pp. 71-99.
The Merck Index 8th Ed. (1968), pp. 105, 455, 467-468, 729, 781, 892, 918-919, 1036, 1037, 1112 and 1113-Merck & Co.
Physician's Desk Reference (PDR)-1968 Ed., pp. 738, 752, 781, 811, 812, 915, 1084, 1104-1129.
Waife et al., Annals of Internal Med. 58 (5) (1963), pp. 810-816.
The Megablastic Anemias-I. C. Hanarin (1969), pp. 923-973 and 994-1000-Blackwell Scientific Publs.
Crosby, William H., (1980), Arch. Intern. Med., vol. 140, Dec. 1980, p. 1582-"Improvisation Revisited-Oral Cyanocobalamin Without Intrinsic Factor For Pernicious Anemia".
The Physicians Desk Reference (PDR) 1989 43rd Ed., p. 624, Edward R. Barnhart Publisher.

*Primary Examiner*—Douglas W. Robinson
*Assistant Examiner*—Raymond J. Henley, III
*Attorney, Agent, or Firm*—Woodard, Emhardt, Naughton, Moriarty & McNett

[57] ABSTRACT

Improved multi-factor hematinic vitamin preparations which provide vitamin $B_{12}$ and folic acid in a one to one ratio and in safe and fully orally effective daily dosage amounts.

6 Claims, No Drawings

SAFE ORAL FOLIC-ACID-CONTAINING VITAMIN PREPARATION

CROSS REFERENCES TO RELATED APPLICATIONS

This application is a continuation of Ser. No. 869,985, filed June 3, 1986, now abandoned. That application was a continuation of Ser. No. 662,813, filed Oct. 22, 1984, now abandoned. That application was a continuation of application Ser. No. 500,228, filed June 1, 1983, now abandoned. That application was a continuation of application Ser. No. 268,744, filed June 1, 1981, now abandoned. That application was a continuation of application Ser. No. 826,814, filed Aug. 22, 1977, now abandoned. That application was a continuation of application Ser. No. 650,887, filed Jan. 21, 1976, now abandoned. That application was a continuation of application Ser. No. 57,302, filed July 22, 1970, now abandoned.

BACKGROUND OF THE INVENTION

Historically, liver was early recognized as superior nutrition for providing factors necessary for the body's production of red blood cells and hemoglobin. Following early studies with liver and liver extracts, intensive investigation over a number of decades of factors found in liver resulted in the isolation of the principal water soluble hematinic vitamins, folic acid (also referred to as vitamin Bc and vitamin M) and vitamin $B_{12}$.

Folic acid was the first of these major hematinic vitamins to be made generally available in pure form. From the beginning the cost of folic acid was relatively low. The vitamin was therefore employed primarily orally and the dosages used were quite high. For example, folic acid was commonly supplied as 5, 10, or 20 mg. tablets and doses as high as 400 mg. were given without ill effects. The only real and serious problem encountered with the use of folic acid was that which followed when it was used for what is now recognized to have been for the wrong purpose, i.e. to treat the so-called pernicious anemia patient. Such a patient, of course, is now known to be one who is really deficient in vitamin $B_{12}$ secondary to his inability to secrete intrinsic factor, and only sometimes, but not necessarily, also deficient in folic acid.

Progressively over the years various investigators have shown that large oral doses are not really necessary to treat simple folic acid deficiency. Indeed as little as 25 micrograms per day orally have in some instances been shown to be minimally effective in patients deficient in this vitamin. The hematological response which can be induced in adults having megaloblastic anemia with oral doses of folic acid in the range of 25 to 250 micrograms, implies that the minimal daily requirement for folate in the adult is within this range.

The National Academy of Science, National Research Council's Food and Nutrition Board's 1968 Recommended Daily Dietary Allowances list indicated pregnancy as the category of highest need for folate, and specifies 800 micrograms from dietary sources as the R.D.A. (Recommended Daily Dietary Allowance) for folate during pregnancy. The Board also recognizes, however, that pure forms of folate may be effective in doses less than one-fourth of the R.D.A. from dietary sources, or in the case of pregnancy at a dose level as low as 200 micrograms per day.

Vitamin $B_{12}$ became available in pure crystalline form several years after folic acid had become available. Unlike folic acid, however, the cost of vitamin $B_{12}$ was initially quite high. Accordingly, the usual recommendations were that the vitamin be given preferentially by the intramuscular route of administration. The minimum parenteral dose was therefore defined early for patients with so-called pernicious anemia. It was shown that very small doses given intramuscularly were dramatically effective in these patients, who, as indicated above, now are recognized as having a vitamin $B_{12}$ deficiency secondary to a deficiency in their gastric mucosa making them unable to produce their own intrinsic factor.

Low microgram quantities of vitamin $B_{12}$ that are effective parenterally were found to be effective orally in the so-called pernicious anemia patient only when given with stomach concentrates. However, the commercially available preparations which contain intrinsic factor from hog stomach were soon found to be unreliable, and plagued with development of resistance to this potentiation of absorption of small microgram amounts of the vitamin. This potential for treatment failure was responsible for the decision by the Food and Drug Administration to place these preparations on prescription status. The unreliability of these preparations was also responsible for the widespread disrepute into which all oral therapy for so-called pernicious anemia fell.

Over the years, however, there have been many published reports that fully document the effecacy and safety of vitamin $B_{12}$ administered in various large amounts without intrinsic factor to patients with so-called pernicious anemia. Indeed it has long been known that when large amounts of vitamin $B_{12}$ are given orally without intrinsic factor, no difference in response can be demonstrated between normal subjects and patients with intrinsic factor deficiency (the so-called pernicious anemia patient). Following the oral administration of 100 to 100,000 micrograms of radioactive vitamin $B_{12}$, approximately the same percentage of the radioactivity administered is detected in the urine of patients with intrinsic factor deficiency and/or normal subjects. Since equal amounts are excreted under these circumstances, equal amounts are also absorbed and estimated to be one percent of the administered dose. From the data of these studies it is known that the oral administration of 500 micrograms of vitamin $B_{12}$ per day provides for the absorption of approximately 5 micrograms of the vitamin. The human daily body requirement for vitamin $B_{12}$ has been estimated to be between 1 and 5 micrograms or, in some exceptional cases slightly higher.

SUMMARY OF THE INVENTION

I have found that vitamin $B_{12}$ and folic acid are best provided in new prophylactic and therapeutic vitamin-hematinic formulations in approximately one to one ratio and in recognized safe and fully orally effective amounts. I have found that formulations in which the folic acid and vitamin $B_{12}$ are present in equal amounts of 500 mcg. each are clinically safe and fully orally effective and I believe these formulations to be the preferred embodiments of the invention. Also a daily dosage of formulations including folic acid and vitamin $B_{12}$ in equal amounts of 1 mg. each have been found to be clinically safe and fully orally effective. In view of the fact that the human daily body requirement of vitamin $B_{12}$ is between one and five mcg. and approximately one percent of orally administered vitamin $B_{12}$ is absorbed in the body, for some patients a daily dosage of a formulation including 100 mcg. of each of folic acid and vitamin $B_{12}$ may be a safe and fully orally effective amount.

The problem with the preparations currently available is best illustrated by an examination of typical formulations. In one of the multivitamin formulations currently being marketed the ingredients are present in the following amounts:

| | |
|---|---|
| Vitamin A (Acetate) | 1.2 mg. |
| Vitamin D | 10 mcg. |
| Vitamin C-Ascorbic Acid | 50 mg. |
| Vilamin $B_1$ | 3 mg. |
| Vitamin $B_2$ | 2 mg. |
| Vitamin $B_6$ -Pyridoxine Hydrochloride | 3 mg. |
| Vitamin $B_{12}$ | 5 mcg. |
| Niacinamide | 10 mg. |
| Calcium Carbonate | 600 mg. |
| Ferrous Sulfate | 150 mg. |

This formulation provides vitamin $B_{12}$ in an amount that is totally inadequate to prevent or treat clinical deficiencies of vitamin $B_{12}$. The formulation contains no folic acid and thus is inadequate in preventing or treating deficiency of these vitamins.

In another widely distributed formulation the ingredients are present in the following amounts.

| | |
|---|---|
| Elemental Iron-Ferrous Fumarate | 100 mg. |
| Surfactant Dioctyl Sodium Sulphosuccinate NF | 100 mg. |
| Vitamin $B_1$ | 7.5 mg. |
| Vitamin $B_2$ | 7.5 mg. |
| Vitamin $B_6$-Pyridoxine Hydrochloride | 7.5 mg. |
| Vitamin $B_{12}$ | 50 mg. |
| Vitamin C-Ascorbic Acid | 50 mg. |
| Niacinamide | 30 mg. |
| Folic Acid | 50 mcg. |
| Pantothenic Acid (as D Panthothenyl Alcohol) | 15 mg. |

This formulation is typical of those that provide vitamin $B_{12}$ in an amount that is totally inadequate to treat clinical deficiencies of the vitamin together with only a minimal amount of folic acid.

A typical hematinic formula contains ingredients as follows:

| | |
|---|---|
| Special Liver-Stomach Concentrate (Containing Intrinsic Factor) | 150 mg. |
| Cobalamin Concentrate, N.F., Equivalent to Cobalamin | 7.5 mcg. |
| Iron, Elemental (As Ferrous Fumarate) | 110 mg. |
| Ascorbic Acid (Vitamin C) | 75 mg. |
| Folic Acid | 1 mg. |

This preparation contains a dangerous folic acid vitamin $B_{12}$ ratio. In addition the vitamin $B_{12}$ is present in such small amounts that it must depend on an intrinsic factor mechanism for absorption. The unreliability of intrinsic factor $B_{12}$ products such as these is widely recognized. Indeed, because of the potential for treatment failure, such preparations are no longer permitted to be distributed over the counter.

My improved formulations provide vitamin $B_{12}$ in a quantity that assures the body of its daily requirement without regard to the ability of the stomach to secrete intrinsic factor for vitamin $B_{12}$. It is thus fully effective in the prophylaxis and treatment of so-called pernicious anemia and eliminates the concerns for the dangers of so-called "masking of pernicious anemia" by folic acid with the resultant potential for neurological damage to the patient, and the resistance problem associated with the use of older, oral vitamin $B_{12}$-intrinsic factor preparations. Indeed, an adequate daily oral dose of vitamin $B_{12}$ that does not depend on intrinsic factor for absorption for example 100 to 1,000 micrograms of vitamin $B_{12}$ constitutes an entirely acceptable alternative to parenteral therapy in all conditions with defective vitamin $B_{12}$ absorption.

Much has been written on the interrelations of vitamin $B_{12}$ and folic acid. Clinically, it is recognized that severe deficiency of either vitamin alone can give rise to macrocytic anemia and megaloblastic maturation arrest in the marrow. In addition, it is recognized that vitamin $B_{12}$ deficiency may also give rise to neurological abnormalities, including damage of peripheral nerves and/or of the posterolateral columns of the spinal cord. It is also recognized that combined deficiencies commonly occur and that the use of either vitamin alone for the treatment of deficiency of the other vitamin may result in only temporary or incomplete patient response. My novel formulations give both vitamins together in amounts demonstrated for each to be fully effective orally whenever deficiency of either vitamin is to be treated or prevented. The dilemma of which of these hematinic vitamins to use first is thus eliminated, the danger of "masking" a case of so-called pernicious anemia is not present.

My novel formulation, containing one tenth to one milligram amounts of both vitamin $B_{12}$ and folic acid, wherein these components are present in an approximate 1 to 1 ratio in safe and fully orally effective amounts provides an insurance against all potential mechanisms for development of deficiency of either vitamin clinically. If a supplement is to provide the insurance that alone justifies its manufacture, availability and recommendation, it must not contain less than an amount that beneficially affects the clinical manifestations of the deficiencies it purports to prevent or treat.

In making available one tenth to one milligram quantities of vitamin $B_{12}$ and folic acid in multiple vitamin preparations I have solved virtually all of the serious problems surrounding these preparations.

A typical multi-factor hematinic vitamin formulation prepared according to my novel invention would preferably be in capsule form in which each capsule contains:

| | |
|---|---|
| Vitamin $B_{12}$ (Crystalline) | 500 mcg. |
| Folic Acid | 500 mcg. |
| Thiamine (Vitamin $B_1$) | about 7.5 mg. to 15 mg. |
| Riboflavin (Vitamin $B_2$) | about 7.5 mg. to 15 mg. |
| Pyridoxine Hydrochloride (Vitamin $B_6$) | |
| Pantothenic Acid | 15 mg. |
| Niacinamide | about 30 mg. to 100 mg. |
| Ascorbic Acid (Vitamin C) | about 200 mg. to 500 mg. |

In addition, other components, such as ferrous fumarate for example, may be added to provide elemental iron in amounts of about 50 to 500 mgs. The term "elemental iron" is intended to refer to the iron component in the ferrous fumarate.

My invention is illustrated by the following specific but non-limiting examples:

EXAMPLE I

A multi-factor hematinic vitamin formulation was prepared in which each capsule contained:

| | |
|---|---|
| Vitamin $B_{12}$ (Crystalline) | 500 mcg. |
| Folic Acid | 500 mcg. |
| Thiamine (Vitamin $B_1$) | 7.5 mg. |
| Riboflavin (Vitamin $B_2$) | 7.5 mg. |
| Pyridoxine Hydrochloride (Vitamin $B_6$) | 7.5 mg. |
| Pantothenic Acid | 15 mg. |
| Niacinamide | 30 mg. |
| Ascorbic Acid (Vitamin C) | 200 mg. |

EXAMPLE II

Desired clinical results were obtained on administration of a hematinic formulation in which each capsule contained:

| | |
|---|---|
| Vitamin $B_{12}$ (Crystalline) | 500 mcg. |
| Folic Acid | 500 mcg. |
| Ascorbic Acid (Vitamin C) | 150 mg. |
| Iron, elemental (as Ferrous Fumarate) | 110 mg. |

EXAMPLE III

Another example of this invention is a hematinic vitamin preparation in which each capsule contains:

| | |
|---|---|
| Vitamin $B_{12}$ (Crystalline) | 500 mcg. |
| Folic Acid | 500 mcg. |
| Thiamine (Vitamin $B_1$) | 15 mg. |
| Riboflavin (Vitamin $B_2$) | 15 mg. |
| Pyridoxine Hydrochloride (Vitamin $B_6$) | 15 mg. |
| Pantothenic Acid | 15 mg. |
| Niacinamide | 100 mg. |
| Ascorbic Acid (Vitamin C) | 500 mg. |

EXAMPLE IV

A multi-factor hematinic vitamin formulation was prepared in which each capsule contained:

| | |
|---|---|
| Vitamin $B_{12}$ (Crystalline) | 500 mcg. |
| Folic Acid | 500 mcg. |
| Thiamine (Vitamin $B_1$) | 7.5 mg. |
| Riboflavin (Vitamin $B_2$) | 7.5 mg. |
| Pyridoxine Hydrochloride (Vitamin $B_6$) | 7.5 mg. |
| Pantothenic Acid | 15 mg. |
| Niacinamide | 30 mg. |
| Ascorbic Acid (Vitamin C) | 200 mg. |
| Elemental Iron (Ferrous Fumarate) | 100 mg. |

FURTHER EXAMPLES

It should be understood that further examples of the intention would include a range of capsule content of between 100 mcg. and 1.0 mg. of vitamin $B_{12}$ (Crystalline) and between 100 mcg. and 1.0 mg. folic acid with the vitamin $B_{12}$ and the folic acid supplied in an approximate one to one ratio. The capsule also would contain other B complex vitamins in the amounts set forth in the examples above.

It should further be understood that any solid oral dosage form of the invention may be used whether a capsule or the equivalent thereof.

The invention claimed is:

1. A method of treating or preventing macrocytic-megaloblastic anemia in humans which anemia is caused by either folic acid deficiency or by vitamin $B_{12}$ deficiency which comprises administering a daily oral dosage of a vitamin preparation to a human in need thereof comprising at least about 0.5 mg. of vitamin $B_{12}$ and at least about 0.5 mg. of folic acid.

2. The method of claim 1 in which the amount of vitamin $B_{12}$ and folic acid administered is in an approximate one to one ratio.

3. The method of claim 1 in which the administering includes administering a solid oral dosage form which comprises at least about 0.5 mg. of vitamin $B_{12}$ and at least about 0.5 mg of folic acid and further comprises a pharmaceutically acceptable iron compound in which the iron component is from 50 to 500 mgs.

4. A method of treating or preventing macrocytic-magaloblastic anemia in humans which anemia is caused by either folic acid deficiency or by vitamin $B_{12}$ deficiency which comprises orally administering combined vitamin $B_{12}$ and folic acid to a human in need thereof in sufficient amounts to achieve an oral administration of at least about 0.5 mg. of vitamin $B_{12}$ and at least about 0.5 mg. of folic acid within one day.

5. The method of claim 4 in which the administering of vitamin $B_{12}$ and folic acid is in an approximate one to one ratio.

6. The method of claim 4 in which the administering includes administering a solid oral dosage form which comprises at least about 0.5 mg. of vitamin $B_{12}$, at least about 0.5 mg. of folic acid and a pharmaceutically acceptable iron compound in which the iron component is from 50 to 500 mgs.

* * * * *